US011305007B2

(12) United States Patent
Ding et al.

(10) Patent No.: US 11,305,007 B2
(45) Date of Patent: Apr. 19, 2022

(54) COMPOSITE MULTI-EPITOPE EXPRESSION CASSETTE, A RECOMBINANT VIRUS COMPOSED THEREOF AND APPLICATION THEREOF

(71) Applicant: SHANGHAI VETERINARY RESEARCH INSTITUTE, CHINESE ACADEMY OF AGRICULTURAL SCIENCES (NATIONAL CENTER FOR ANIMAL HEALTH SHANGHAI), Shanghai (CN)

(72) Inventors: Chan Ding, Shanghai (CN); Huabin Shao, Shanghai (CN); Lei Tan, Shanghai (CN); Guoyuan Wen, Shanghai (CN); Shengqing Yu, Shanghai (CN); Xusheng Qiu, Shanghai (CN); Ying Liao, Shanghai (CN); Chunchun Meng, Shanghai (CN); Yingjie Sun, Shanghai (CN); Cuiping Song, Shanghai (CN)

(73) Assignee: SHANGHAI VETERINARY RESEARCH INSTITUTE, CHINESE ACADEMY OF AGRICULTURAL SCIENCES (NATIONAL CENTER FOR ANIMAI HEALTH SHANGHAI), Shanghai (CN)

( * ) Notice: Subject to any disclaimer, the term of this patent is extended or adjusted under 35 U.S.C. 154(b) by 433 days.

(21) Appl. No.: 16/495,502

(22) PCT Filed: Jan. 21, 2019

(86) PCT No.: PCT/CN2019/072459
§ 371 (c)(1),
(2) Date: Sep. 19, 2019

(87) PCT Pub. No.: WO2019/205753
PCT Pub. Date: Oct. 31, 2019

(65) Prior Publication Data
US 2021/0338802 A1 Nov. 4, 2021

(30) Foreign Application Priority Data
Apr. 27, 2018 (CN) .................. 201810394542.X

(51) Int. Cl.
| | |
|---|---|
| *A61K 39/00* | (2006.01) |
| *A61K 39/12* | (2006.01) |
| *A61K 48/00* | (2006.01) |
| *C12N 7/00* | (2006.01) |
| *C12N 15/86* | (2006.01) |
| *A61K 39/215* | (2006.01) |
| *A61P 31/14* | (2006.01) |
| *C07K 14/005* | (2006.01) |

(52) U.S. Cl.
CPC ............ *A61K 39/215* (2013.01); *A61P 31/14* (2018.01); *C07K 14/005* (2013.01); *C12N 15/86* (2013.01); *A61K 2039/552* (2013.01); *A61K 2039/70* (2013.01); *C07K 2319/00* (2013.01); *C12N 2760/18134* (2013.01); *C12N 2760/18144* (2013.01); *C12N 2770/20022* (2013.01); *C12N 2770/20034* (2013.01)

(58) Field of Classification Search
CPC ........ C07K 14/005; C12N 7/00; C12N 15/86; A61K 2039/53; A61K 39/12
See application file for complete search history.

(56) References Cited

FOREIGN PATENT DOCUMENTS

| | | |
|---|---|---|
| CN | 1609213 | 4/2005 |
| CN | 103387604 | 11/2013 |
| CN | 104548088 | 4/2015 |
| CN | 105420261 | 3/2016 |
| CN | 105949321 | 9/2016 |
| CN | 106390112 | 2/2017 |
| CN | 107287218 | 10/2017 |
| CN | 107893057 | 4/2018 |
| CN | 108546302 | 9/2018 |

OTHER PUBLICATIONS

Chinese Office Action cited in 201810394542.X dated Feb. 25, 2021.
European Search Report issued in 19759487.2-1110 / 3592779 dated Dec. 11, 2020.

(Continued)

*Primary Examiner* — Barry A Chestnut
(74) *Attorney, Agent, or Firm* — Workman Nydegger

(57) ABSTRACT

The present application relates a composite multi-epitope expression cassette, a recombinant virus composed thereof and application thereof, and in particular to a chimeric recombinant Newcastle disease virus inserted with an IBV epitope cassette and a vaccine prepared by using the virus. The expression cassette comprises: (a) T cell epitopes derived from S1 proteins of avian infectious bronchitis virus Holte strain and avian infectious bronchitis virus QX-like strain; and (b) B cell epitopes derived from S1 protein of avian infectious bronchitis virus Australian T strain. In the present application, the multi-epitope chimeric ST/B gene of avian infectious bronchitis virus is inserted into the backbone of LaSota strain, so that the LaSota strain can express S1-T/B protein. Thus, the purpose of preventing both ND and IB diseases is achieved. In addition, the T cell epitopes and B cell epitopes act synergistically to produce an earlier and more comprehensive immune response against virus.

12 Claims, 4 Drawing Sheets
Specification includes a Sequence Listing.

(56) References Cited

OTHER PUBLICATIONS

Zhao, Wei, et al., "Newcastle Disease Virus (NDV) Recombinants Expressing Infectious Laryngotracheitis Virus (ILTV) Glycoproteins gB and gD Protect Chickens against ILTV and NDV Challenges", Journal of Virology p. 8397-8406, Aug. 2014, vol. 88 No. 15.

Wen, Guoyuan, et al., "Molecular basis for the thermostability of Newcastle disease virus", Scientific Reports, Mar. 3, 2016.

Tan, Lei, et al., "A Recombinant La Sota Vaccine Strain Expressing Multiple Epitopes of Infectious Bronchitis Virus (IBV) Protects Specific Pathogen-Free (SPF) Chickens against IBV and NDV Challenges" Nov. 1, 2019, *Vaccines* 2019.

Tan, Lei, et al., "Development of a Recombinant Thermostable Newcastle Disease Virus (NDV) Vaccine Express Infectious Bronchitis Virus (IBV) Multiple Epitopes for Protecting against IBV and NDV Challenges", Oct. 1, 2020, *Vaccines* 2020.

Wen, Guoyuan, et al., "Development of a novel thermostable Newcastle disease virus vaccine vector for expression of a heterologous gene", Jan. 20, 2015, *Journal of General Virology* (2015), 96, 1219-1228.

Tan, L. et al., "Infectious bronchitis virus poly-epitope-based vaccine protects chickens from acute infection" Vaccine, Sep. 21, 2016, vol. 34.

Tan, L. et al., "Prediction and identification of novel IBV S1 protein derived CTL epitopes in chicken", Vaccine, Nov. 25, 2015, vol. 34.

International Search Report cited in PCT/CN2019/072469 dated Jan. 21, 2019.

COMPOSITE MULTI-EPITOPE EXPRESSION CASSETTE, A RECOMBINANT VIRUS COMPOSED THEREOF AND APPLICATION THEREOF

TECHNICAL FIELD

The present application relates to the field of gene and protein engineering, in particular to a composite multi-epitope expression cassette, a recombinant virus composed thereof and application thereof, and in particular to a chimeric recombinant Newcastle disease virus inserted with an IBV epitope cassette and a vaccine prepared by using the virus.

BACKGROUND

ND (newcastle disease) is an acute, highly lethal avian disease that is ordered by the World Organisation for Animal Health (OIE) to be reported. The pathogen of ND is New Castle disease virus (NDV), which is a member of the Avulavirus genus in the Paramyxoviridae family. NDV is a single-stranded negative-sense RNA virus with a genome full-length of approximately 15.8 kb, including six open reading frames encoding nuclear protein (NP), phosphoprotein (P), matrix protein (M), fusion protein (F), Hemagglutinin-neuraminidase (HN) and large polymerase protein (L), respectively.

According to differences in virulence, NDV can be divided into velogenic strains, mesogenic strains and lentogenic strains. Velogenic strains can cause acute, lethal infections in poultry with a high mortality rate. Lentogenic strains only cause mild respiratory infections or intestinal infections and thus are widely used in the production of Newcastle disease live vaccines. Among the numerous NDV live vaccines, the low-virulence live vaccines represented by LaSota strain and Clone30 strain are widely used in China because of their convenient use and low side effects. The LaSota strain has been approved for use as a vaccine strain in Europe in the early 1970s, and hereafter Newcastle disease virus vaccines produced from this strain have been widely used worldwide. However, low-virulence live vaccines have poor heat resistance and high requirements for refrigeration conditions, and vaccination failures may occur sometimes due to inappropriate storage or use of vaccines.

Currently, the vaccines that have been approved for the prevention and treatment of Newcastle disease (ND) and avian infectious bronchitis (IB) are mostly bivalent inactivated vaccines or single vaccines. CN104548088A discloses a method for preparing a bivalent vaccine which uses recombinant Newcastle disease virus LaSota strain expressing the avian infectious bronchitis virus (IBV) spike protein subunit 1 multi-epitope cassette. This antibody can prevent both chicken Newcastle disease and chicken nephropathogenic IBV infection. However, the clinical production therefor has a lot of shortages: it can not induce cellular immune response, use of large doses and need for cooperation with an adjuvant, complicated preparation process and high production costs, and two or more booster immunizations are needed to effectively trigger the production of neutralizing antibodies even when an inactivated whole virus vaccine is used. In addition, the avian IBV has many serotypes and cross-protection between different serotypes is poor. A single serotype of attenuated or inactivated vaccine can only protect the host from being infected with the same serotype virus, with low or no protection against other serotypes of IBV.

Since the first reverse genetic system (RGS) for NDV have been established by European scholars in 1999, this technology has now been successfully applied to researches on pathogenicity, replication regulation mechanism and vaccine vectors of NDV. In particular, immunogenic genes can be inserted at different sites in genome of NDV lentogenic vaccine strain which is used as a vaccine vector and expressed, and high levels of genetic and expression stability are still maintained after successive multiple passages in cells or chicken embryos. Many immunogenic genes of avian pathogens, such as the HA gene of avian influenza virus, the VP2 gene of chicken infectious bursal disease virus and the S2 gene of avian infectious bronchitis etc., have been highly expressed in NDV vectors, and better immune protection effects have been achieved. However, most of the current RGS studies for NDV are limited to non-heat-resistant strains, and the establishment of RGS for heat-resistant strains has rarely been reported.

IB is one of the poultry List B infectious diseases prescribed by OIE and China. This disease is an acute, highly contagious and economically significant viral disease caused by IBV. IBV belongs to the Coronavirus family and is a representative strain of coronavirus. S protein is the main component of fibers on the outermost layer of coronavirus, consisting of two parts, S1 and S2. The main cell epitopes of IBV are existed on S1 protein that is the main protein that determines the serum-specific antigenic determinant of IBV. Due to the numerous serotypes of IBV, S1 is the most mutated gene of IBV. The nucleotide variation in S1 gene of different strains can be up to 50% or more, and there are 25%-50% amino acid differences in S1 gene of the same serum strain. These differences lead to weak cross-protection between strains. Therefore, IBV vaccines that are restricted to a particular subtype may not provide a complete protection, while bi- or multi-combined vaccines that are prepared by using multiple IBV subtypes have an unsatisfactory effect due to autoantigen cross-reaction interference resulted from multiple antigens. IBV occurs in all countries where poultry is kept, and the pathogen thereof has multiple clinical phenotypes including nephropathogenic, respiratory type and glandular type, and often cause a mixed infection with NDV, AIV and other viruses, which brings great difficulties to the prevention and control of this disease. At present, these three subtypes of infectious bronchitis virus have been found in chicken farms in China.

The IBV vaccines used in market are mainly live virus vaccines and inactivated virus vaccines with oil adjuvant. Live virus vaccines are mainly used for early protection or primary immunization of chicks, and inactivated vaccines are generally used for booster immunization. Because the IBV is very easily to be inactivated, field trials often fail as a result of ineffectiveness of the vaccine. In additional, conventional vaccines only protect a single subtype of IBV and do not produce a cross-immunoprotective effect. Therefore, it is urgent and necessary to develop a general vaccine that protects several subtypes of IBV.

With the in-depth studies of antigen epitopes of pathogens, epitope-based vaccines have begun to show good application prospects. The most important for a multi-epitope vaccine is the acquisition of a protective antigen gene which is composed of several antigenic determinants, also known as antigen epitopes. Antigen epitope is the exact component that stimulates immune cells to produce an immune response. Depending on the cell to which the antigen receptor binds, antigen epitopes are divided into T cell epitopes and B cell epitopes. The T cell epitope is mainly presented on the cell surface of an antigen presenting cell (APC) after binding to MHC molecule and bind to TCR to activate a T cell immune response. MHC Class I molecules mainly bind to 8-10 amino acid polypeptides, while MHC Class II molecules mainly bind 12-25 amino acid polypeptides. The B cell epitope is different from T cell epitope in structure, and includes two forms, non-continuous conformational epitope and continuous linear epitope, both exhibit no MHC restriction. B cell epitopes are relatively long, ranging from more than 10 amino acids to more than 100 amino acids. They exert an antiviral effect by binding to BCR to activate B lymphocyte to secrete antibodies. A practical method to improve the immune protection effect of a vaccine is construction of a monovalent or multivalent vaccine on the basis of a protective antigen epitope which is selected by screening potential antigen epitopes. The screened functional epitope vaccine can not only avoid the immunosuppressive effect induced by inhibitory epitopes, but also predominate the immune response induced by protective epitopes.

Chicken MHC is located on chromosome 16, consisting of two gene regions, B and Y sites. The B region includes three gene groups: B-F, B-L and B-G. The antigens encoded by B-F and B-L are identical to mammalian MHC Class I and II molecules in structure and function, respectively. The B-F gene is further divided into two types, B-F1 and B-F2. The chicken B-F2 gene is mainly responsible for presenting endogenous antigenic peptides to CD8+ T cells for recognition to induce a cellular immune response. The MHC I molecular haplotype corresponds to a specific type with a specific polypeptide amino acid anchor site. Only the corresponding type can recognize the specific polypeptide amino acid sequence. This polypeptide sequence binds to a specific MHC Class I molecule haplotype to form a polypeptide-MHC I molecule complex that will be presented on cell surface for recognition by T cell receptor (TCR). After the recognition, killer T lymphocytes are activated to produce a cell killing effect, thus a cellular immune response is created.

At present, the researches on B cell antigen epitopes of IBV are mainly concentrated on N protein and M protein, and reports on B cell antigen epitopes of S protein is relatively less. Differences in amino acids of the S protein of different types of infectious bronchitis virus are mainly concentrated in the S1 protein region. It is inferred that the hypervariable region may be the B cell antigen epitope region of S1 protein. Studies have shown that the B cell antigen epitopes of most IBVs are located at the N-terminus of S1 protein, and differences in amino acids of S protein of different strains are also concentrated in the following three regions of S1: N-terminal amino acids 37-83, containing two hydrophilic regions; amino acids 117-160, being a hydrophobic region; amino acids 269-298, being a strong hydrophilic region. These regions are all inferred to be the antigen epitopes on S1 protein, and amino acids 294-316, 532-537 and 548-566 may also have effects on protection. Unlike a B cell epitope, the T cell epitope of chicken is restricted strictly by species MHC and is primarily closely related to the binding motif of chicken B-F2 haplotype.

At present, there are few studies on T cell epitopes of IBV. Based on the above analysis, how to find a recombinant NDV with good thermal stability, high virus titer, good genetic stability, strong immunogenicity and long immune protection period is a problem that needs to be solved urgently.

SUMMARY OF THE INVENTION

The purpose of the present application is to provide a composite multi-epitope, a recombinant virus comprised thereof and application thereof. The virus and vaccine can cause high levels of cellular and humoral responses in chickens, and can produce a complete protection against a challenge of a lethal dose of avian infectious bronchitis virus.

In order to achieve the purpose of this present application, the present application adopts the following technical solutions:

In a first aspect, the application provides a composite multi-epitope expression cassette comprising:

(a) T cell epitopes derived from S1 proteins of avian infectious bronchitis virus Holte strain and avian infectious bronchitis virus QX-like strain; and (b) B cell epitopes derived from S1 protein of avian infectious bronchitis virus Australian T strain.

In the present application, the applicant has aligned the amino acids of S1 genes of IBV M41 strain, Australian T strain and QX-like ck/CH/TS/201012 strain based on the binding motifs of MHC Class I molecules of chicken haplotypes B-F2*04 (BF04), B-F2*12 (BF12), B-F2*15 (BF15) and B-F2*19 (BF19) to screen CD8$^+$ T cell epitopes of IBV S1 protein that correspond to the binding motifs. The screened functional epitope vaccine not only avoids the immunosuppressive effects induced by inhibitory epitopes, but also predominates the immune response induced by protective epitopes. The constructed recombinant IBV multi-epitope chimeric S-T/B gene rNDV-IBV-T/B strain can protect both NDV and multiple subtypes of IB. Amplification of recombinant NDVs is dependent on chicken embryos. The virus has the characteristics of high titer, good genetic stability, strong immunogenicity and long immune protection period, and has good thermal stability, which makes it more suitable for transportation and storage.

Moreover, the applicant has also discovered that by inserting T cell epitopes and B cell epitopes simultaneously into a recombinant virus, the T cell epitopes and B cell epitopes can act synergistically to produce an earlier and more comprehensive immune response against virus compared to a recombinant virus containing T cell epitopes or B cell epitopes alone.

According to the present application, the T cell epitopes have amino acid sequences as shown in SEQ ID NOs. 1-4, specifically:

the amino acid sequence as shown in SEQ ID NO. 1 is GAYAVVNV;

the amino acid sequence as shown in SEQ ID NO. 2 is SRIQTATQP;

the amino acid sequence as shown in SEQ ID NO. 3 is SRIQTATDP;

the amino acid sequence as shown in SEQ ID NO. 4 is SRNATGSQP.

According to the present application, the B cell epitopes have amino acid sequences as shown in SEQ ID NOs. 5-7, specifically:

the amino acid sequence as shown in SEQ ID NO. 5 is NYVYYYQSAFRPSGGWHLHG-GAYAVVNVSQETSNAGS;

the amino acid sequence as shown in SEQ ID NO. 6 is RIAAMKQGGNGPSDLFY;

the amino acid sequence as shown in SEQ ID NO. 7 is QTYQTQTAQSGYYNFNFSFLSGFVYKEFNFMYGSYH PKCNFRPENINNGLWFNSLSVSLAY GPLQGGCKQSVFHGRATCCYAY-SYLGPRLCKGVYSGELTQQFECGL.

In the present application, the order of cell epitopes in T cell epitopes and B cell epitopes is not limited. The applicant has found that an order adjustment will not have much impact on the effects of virus. Therefore, the T cell epitopes and B cell epitopes whose order has been adjusted are also within the scope of the present application. Those skilled in the art can adjust the order of T cell epitopes and B cell epitopes according to requirements.

According to the present application, different epitopes among the T cell epitopes and the B cell epitopes are linked by a flexible small molecule linker.

According to the present application, the flexible small molecule linker is KAA, AAY, AAA, GAAA, KAAA, and has the nucleotide sequence as shown in SEQ ID NOs. 8-12, specifically:

the amino acid sequence indicated by KAA (SEQ ID NO. 8) is AAAGCTGCT;

the amino acid sequence indicated by AAY (SEQ ID NO. 9) is GCCGCATAC;

the amino acid sequence indicated by AAA (SEQ ID NO. 10) is GCTGCCGCC;

the amino acid sequence indicated by GAAA (SEQ ID NO. 11) is GGCGCAGCAGCC;

the amino acid sequence indicated by KAAA (SEQ ID NO. 12) is AAAGCAGCCGCA.

In the present application, the flexible small molecule linker used between T cell epitopes and B cell epitopes can be selected as needed. The connection order or selection of these flexible small molecule linkers will not have too much impact on the recombinant virus itself. Those skilled in the art can select a flexible small molecule linker to connect the T cell epitope and the B cell epitope according to requirements, and it is not particularly limited herein.

According to the present application, an enzyme cleavage site is further included in front of and behind the expression cassette, which is any one of Spe I, Xho I, BamH I, EcoR I, Nde I, Pst I or Xho I, preferably is Spe I and Xho I;

According to the present application, a KOZAK sequence which has an nucleotide sequence as shown in SEQ ID NO. 13 specifically GCCACCATG, is further included behind the cleavage site that is located in front of the expression cassette.

According to the present application, the insertion of a flexible small molecule linker, a cleavage site or a KOZAK sequence does not affect the stability and pathogenicity of virus.

According to the present application, the expression cassette has the amino acid sequence as shown in SEQ ID NO. 14, specifically

MGNYVYYYQSAFRPSGGWHLHGGAYAVVNVSQETSNAGSGGGGSGGGGSGG

GGSRIAAMKQGGNGPSDLFYGGGGSGGGGSGGGGSQTYQTQTAQSGYYNFN

FSFLSGFVYKEFNFMYGSYHPKCNFRPENINNGLWFNSLSVSLAYGPLQGG

CKQSVFHGRATCCYAYSYLGPRLCKGVYSGELTQQFECGLTSNFDLLKLAG

DVESNPGPFFFMQVQIQSLFLLLLWVPGSRGKAAGAYAVVNVAAASRIQTA

TQPAAYSRNETDSQPGAAASRNATGSQPKAAGAYAVVNVAAASRIQTATQP

AAYSRNETDSQPGAAASRNATGSQP;

According to the present application, the expression cassette has the nucleotide sequence as shown in SEQ ID NO. 15, specifically

ACGGGTAGAAAGCTTGCCACCATGGGAAATTACGTTTACTACTACCAAGT

GCCTTCAGACCATCAGGTGGTTGGCATTTACATGGAGGTGCTTATGCAGTA

GTAAATGTTTCGCAAGAAACCAGTAATGCAGGAAGCGGAGGCGGAGGCTCC

GGAGGAGGAGGCTCCGGAGGCGGAGGGTCTCGTATTGCTGCCATGAAGCAA

GGCGGTAATGGGCCTAGTGATTTATTTTATGGAGGCGGAGGCTCCGGAGGA

GGAGGCTCCGGAGGCGGAGGGTCTCAAACTTATCAAACACAAACAGCTCAG

AGTGGTTATTATAATTTTAACTTCTCATTTCTGAGTGGTTTTGTGTATAAG

GAGTTTAATTTTATGTATGGTTCTTATCACCCAAAGTGTAATTTTAGACCA

GAAAACATTAATAATGGCCTCTGGTTTAATTCACTTTCAGTTTCGCTTGCG

TATGGCCCTCTTCAAGGCGGCTGCAAGCAATCTGTCTTTCATGGTAGAGCA

ACTTGCTGTTATGCCTACTCCTATTTAGGTCCTAGGTTATGTAAAGGTGTT

TATAGTGGTGAGTTAACACAGCAGTTTGAATGTGGACTGACTAGTAACTTT

GACCTGCTCAAGTTGGCAGGAGACGTCGAGTCCAACCCTGGGCCTTTCTTC

TTCATGCAGGTGCAGATCCAGAGCCTGTTTCTGCTCCTCCTGTGGGTGCCC

GGCTCCAGAGGAAAAGCTGCTGGTGCATATGCAGTCGTCAACGTTGCTGCC

GCCAGTAGGATTCAGACGGCTACTCAGCCGGCCGCATACAGTAGAAATGAG

ACCGATAGTCAGCCGGGCGCAGCAGCCAGTAGAAACGCTACTGGTAGTCAA

CCGAAAGCTGCTGGTGCATATGCAGTCGTCAACGTTGCTGCCGCCAGTAGG

ATTCAGACGGCTACTCAGCCGGCCGCATACAGTAGAAATGAGACCGATAGT

CAGCCGGGCGCAGCAGCCAGTAGAAACGCTACTGGTAGTCAACCGTAATAA

TTAAGAAAAAAT.

In a second aspect, the present application provides a composite multi-epitope comprising the composite multi-epitope expression cassette as described in the first aspect.

According to the present application, the composite multi-epitope is based on Newcastle disease virus LaSota strain as a backbone.

According to the present application, the composite multi-epitope expression cassette is inserted between the M gene and the F gene of Newcastle disease virus LaSota strain.

According to the present application, the HN gene in Newcastle disease virus LaSota strain is replaced with the HN gene in Newcastle disease virus TS09-C strain.

In order to improve the thermal stability of the NDV (New Castle disease virus, NDV) virus vector live vaccine, in the present application the hemagglutinin neuraminidase (HN) gene of LaSota strain has been replaced with the HN gene of heat-resistant lentogenic TS09-C strain. As a result, the thermostability of the recombinant virus has been significantly enhanced. In addition, an exogenously expressed gene can also been inserted into the recombinant NDV vector without enhancing the virulence of the parent virus strain, and the virus titer is stable.

According to the present application, the HN gene in Newcastle disease virus TS09-C strain has the amino acid sequence as shown in SEQ ID NO. 16, and the nucleotide sequence as shown in SEQ ID NO. 17, specifically:

the amino acid sequence as shown in SEQ ID NO. 16 is

MDRAVSQVALENDEREAKNTWRLVFRIAILLSTVVTLAISAAALAYSMEAS

TPSDLVGIPTAISRAEEKITSALGSNQDVVDRIYKQVALESPLALLNTEST

IMNAITSLSYQISGAASSSGCGAPIHDPDYIGGIGKELIVDDASDVTSYYP

SAFQEHLNFIPAPTTGSGCTRMPSFDMSATHYCYTHNVILSGCRDHSHSHQ

YLALGVLRTSATGRVFFSTLRSINLDDTQNRKSCSVSATPLGCDMLCSKVT

-continued

ETEEEDYNSAIPTSMVHGRLGFDGQYHEKDLDVTTLFEDWVANYPGVGGGS

FIDNRVWFPVYGGLKPNSPSDTAQEGKYVIYKRYNDTCPDEQDYQIQMAKS

SYKPGRFGGKRVQQAVLSIKVSTSLGEDPVLTVPPNTVTLMGAEGRVLTVG

TSHFLYQRGSSYFSPALLYPMIVSNKTATLHSPYTFNAFTRPGSVPCQASA

RCPNSCVTGVYTDPYPLVFYRNHTLRGVFGTMLDDKQARLNPVSAVFDSIS

RSRITRVSSSSTKAAYTTSTCFKVVKTNKTYCLSIAEISNTLFGEFRIVPL

LVEILKDDGVREARSSRLSQLREGWKDDIVSPIFCDAKNQTEYRHELESYA

ASWP;

the nucleotide sequence as shown in SEQ ID NO. 17 is

ACGGGTAGAACGGTCGGGGAGGCCGTCCCTCAATCGGGAGCCGGGCCTCAC

AACATCCGTTCTACCGCATCACCAATAGCAGTTTTCAGTCATGGACCGCGC

AGTTAGCCAAGTTGCGCTAGAGAATGATGAAAGAGAGGCAAAGAATACATG

GCGCTTGGTATTCCGGATCGCAATCCTACTCTCAACGGTGGTGACCTTAGC

CATCTCTGCAGCCGCCCTTGCATATAGCATGGAGGCCAGCACACCTAGCGA

TCTTGTAGGCATACCGACTGCGATCTCTAGAGCAGAGGAAAAGATTACATC

TGCACTCGGTTCCAATCAAGATGTAGTAGATAGGATATATAAGCAGGTGGC

CCTCGAATCTCCACTGGCATTGCTAAACACCGAATCTACAATTATGAACGC

AATAACGTCTCTCTTATCAAATCAGTGGGGCCGCAAGTAGCAGCGGATG

TGGAGCACCCATTCATGATCCAGATTATATTGGAGGAATAGGTAAAGAACT

TATTGTAGATGATGCTAGCGACGTCACATCATACTATCCCTCTGCGTTCCA

AGAACACCTGAACTTTATCCCGGCGCCTACTACAGGATCAGGTTGCACTCG

GATGCCCTCATTTGACATGAGCGCTACCCACTACTGTTATACTCACAATGT

GATATTATCTGGCTGCAGAGATCACTCGCACTCACATCAATATTTAGCACT

TGGTGTGCTTCGGACATCTGCAACAGGGAGGGTATTCTTTTCCACTCTGCG

TTCCATCAATCTGGATGACACCCAAAATCGGAAGTCTTGCAGTGTGAGTGC

AACCCCCTTGGGTTGTATATGCTGTGCTCTAAAGTCACAGAGACTGAAGA

AGAGGATTATAACTCAGCTATCCCCACGTCGATGGTACATGGAAGGTTAGG

GTTCGACGGCCAATACCACGAGAAGGACCTAGATGTCACAACACTATTCGA

GGACTGGGTGGCAAACTACCCAGGAGTAGGAGGCGGGTCTTTTATTGACAA

CCGCGTATGGTTCCCAGTTTACGGAGGGCTAAAACCCAATTCGCCCAGTGA

CACCGCACAAGAAGGGAAATATGTAATATACAAGCGATACAATGACACATG

TCCAGATGAGCAAGATTATCAGATTCAAATGGCTAAGTCTTCATATAAGCC

TGGGCGGTTTGGAGGGAAACGCGTACAGCAGGCCGTCTTATCTATCAAAGT

GTCAACATCCTTGGGCGAGGACCCGGTGCTGACTGTACCGCCCAACACAGT

AACACTCATGGGGCCGAAGGCAGAGTTCTCACAGTAGGGACATCTCATTT

CCTTTATCAGCGAGGGTCATCATACTTCTCCCCTGCCCTACTATATCCTAT

GATAGTCAGCAACAAAACAGCCACTCTTCATAGTCCTTATACATTCAATGC

CTTCACTCGACCAGGTAGTGTCCCTTGCCAGGCTTCAGCAAGATGCCCTAA

CTCATGTGTTACCGGAGTCTATACTGATCCATATCCCTTGGTCTTCTATAG

GAACCACACCTTGCGAGGGGTATTCGGGACGATGCTTGATGATAAACAAGC

AAGACTCAACCCTGTATCTGCAGTATTTGACAGCATATCCCGCAGTCGCAT

AACCCGGGTGAGTTCAAGCAGCACCAAGGCAGCATACACAACATCAACATG

TTTTAAAGTTGTAAAGACCAATAAAACCTATTGTCTCAGCATTGCCGAAAT

ATCCAATACCCTCTTCGGGGAATTCAGAATCGTCCCTTTACTAGTTGAGAT

TCTCAAGGATGATGGGGTTAGAGAAGCCAGGTCTAGCCGGTTGAGTCAACT

GCGAGAGGGTTGGAAAGATGACATTGTATCACCTATCTTTTGCGACGCCAA

GAATCAAACTGAATACCGGCACGAGCTCGAGTCCTACGCTGCCAGTTGGCC

ATAATCAGCTAGTGCTAATGTGATTAGATTAAGTCTTGTCGGTAGTCACTT

GATTAAGAAAAAA.

In a third aspect, the present application provides a gene encoding the composite multi-epitope expression cassette as described in the first aspect or the composite multi-epitope as described in the second aspect.

In a fourth aspect, the present application provides a recombinant virus comprising the gene as described in the third aspect.

In a fifth aspect, the present application provides a composite multi-epitope vaccine comprising the recombinant virus as described in the fourth aspect.

In the present application, the NDV attenuated vaccine can simultaneously induce the formation of a systemic humoral immune response, a local mucosal immune response and a cellular immune response, providing more comprehensive and reliable protection to the body; the NDV can proliferate and express antigen genes in a long period in vivo, and thus can induce a long-lasting protective effect; the NDV vaccine can be administrated by many manners including oral water, spray, nasal drops, eye drops or injection, which is very convenient to use; the attenuated NDV has a characteristic of high titer growth in chicken embryos, and thus has low production costs; the NDV is genetically stable and has only one serotype, and there is little possibility of occurrence of virulence reversion and recombination between strains; the replication process is completed in cytoplasm, from RNA to RNA, without a DNA stage, thus there is no possibility of integration into host cell DNA and no risk of artificial transgene; the NDV can not replicate in normal human cells and is generally non-infectious to humans; the NDV, especially an lentogenic strain, is safe for humans and highly reliable in animal food safety.

In a sixth aspect, the present application provides use of the gene as described in the third aspect, the recombinant virus as described in the fourth aspect or the composite multi-epitope vaccine as described in the fifth aspect for the manufacture of a medicament for treatment of Newcastle disease and/or avian infectious bronchitis.

In a seventh aspect, the present application provides use of the gene as described in the third aspect, the recombinant virus as described in the fourth aspect or the composite multi-epitope vaccine as described in the fifth aspect for the treatment of Newcastle disease and/or avian infectious bronchitis.

Compared with the prior art, the present application has the following beneficial effects:

(1) In the present application, the multi-epitope chimeric ST/B gene of avian infectious bronchitis virus is inserted into the backbone of LaSota strain, so that the LaSota strain can express S1-T/B protein. Thus, the purpose of preventing both ND and IB diseases is achieved. In addition, the T cell epitopes and B cell epitopes can act synergistically to produce an earlier and more comprehensive immune response against virus.

(2) In the present application, the HN gene of lentogenic TS09-C strain is replaced with that of the LaSota vaccine strain, increasing the thermal stability of LaSota strain without increasing its pathogenicity, and reducing the requirements for vaccine storage conditions and prolonging the shelf life.

(3) The production cost of the vaccine of the present application is 30% lower than that of the inactivated vaccine. The immunization route is nose drops and eye drops, which saves time and effort compared with inactivated vaccines. Compared with ND and IB single vaccines, the recombinant NDV vector live vaccine (rNDV-IBV-T/B) strain expressing IBV S1 protein T/B multi-epitope can reduce the number of immunizations more than 2 and can effectively control the prevalence and occurrence of these two respiratory infections. This will save direct economic benefits for vaccine use by about 80 million to 100 million CNY/year when calculated on the basis of inoculation of 1 billion chickens per year.

FIGURE LEGEND

FIG. 1 is a schematic diagram of construction of a viral infectious clone of the present application, wherein the target gene 1 is HN gene of TS09-C strain; the target gene 2 is IBV S1 gene T/B cell multi-epitope gene cassette; T7 RNA polymerase promoter sequence; IRL: internal long repeat; TRL: terminal long repeat; TRS: terminal short repeat; IRS: internal short repeat;

FIG. 2 (A) shows the restriction enzyme digestion of a plasmid expressing NP (nuclear protein); FIG. 2 (B) shows the restriction enzyme digestion of a plasmid expressing P (phosphoprotein); FIG. 2 (C) shows the restriction enzyme digestion of a plasmid expressing L (large polymerase protein);

Figures 5A, 5B, 6:
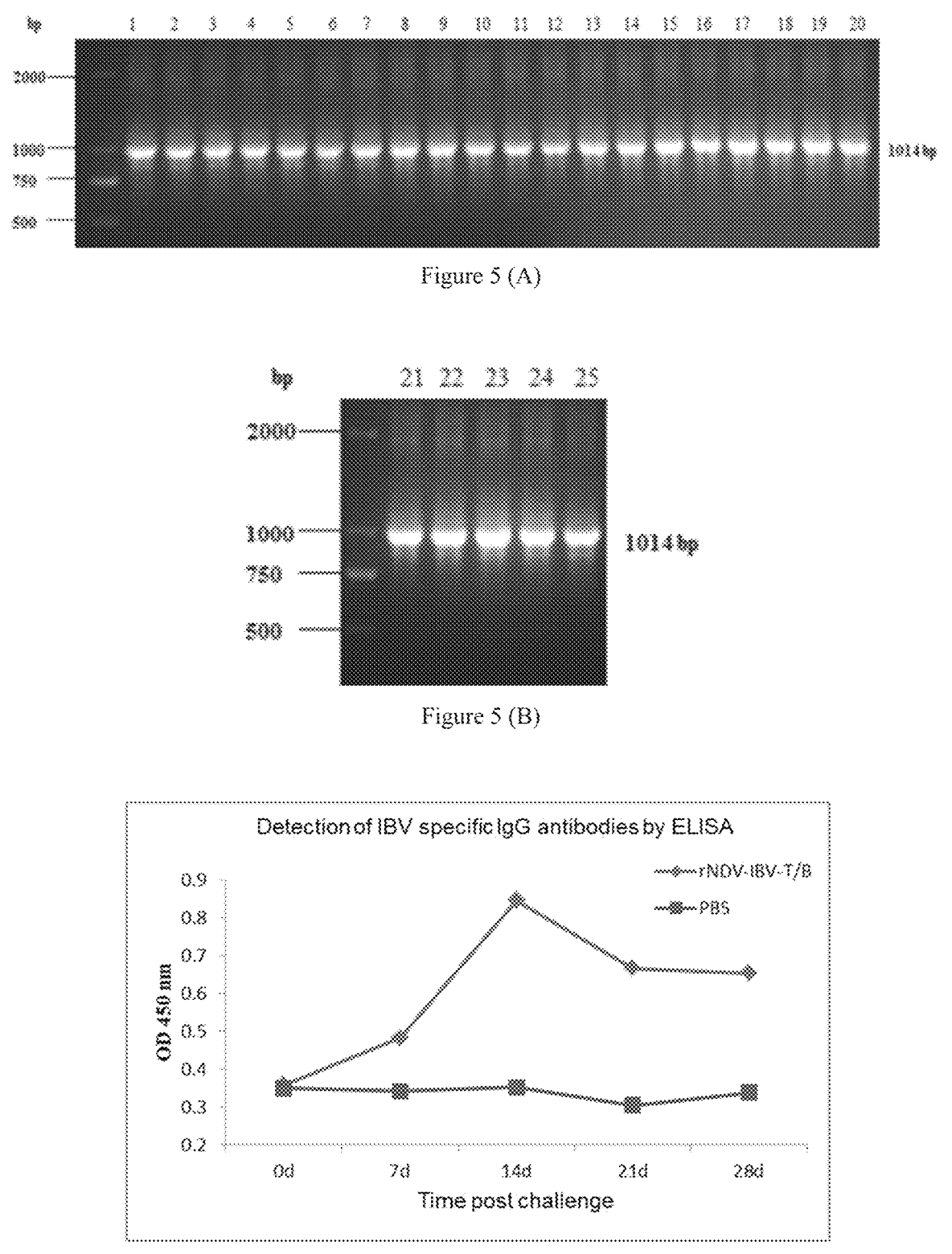
Figure 3:
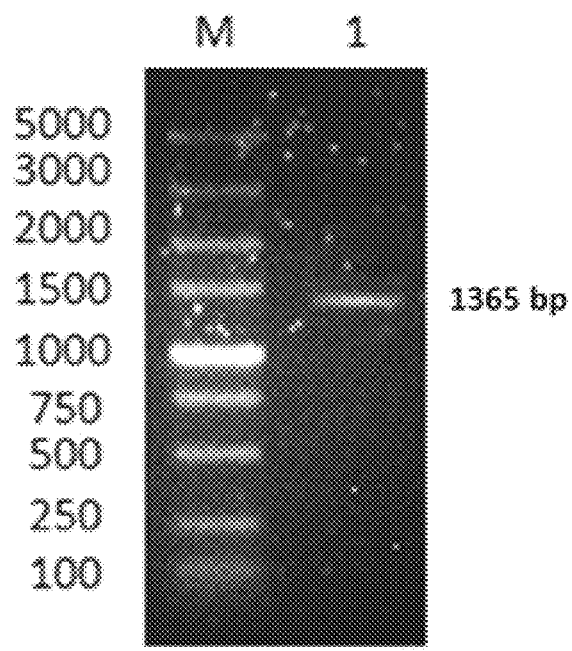
FIG. 3 shows PCR identification results of the recombinant Newcastle disease virus inserted with a IBV-T/B epitope cassette gene of the present application.

FIG. 5 (A) and FIG. 5 (B) show PCR identification results of episode cassette gene of the recombinant virus rNDV-IBV-T/B after 25 passages;

FIG. 6 shows detection of NDV-specific IgG antibodies by ELISA after immunization;

Figures 7, 8:
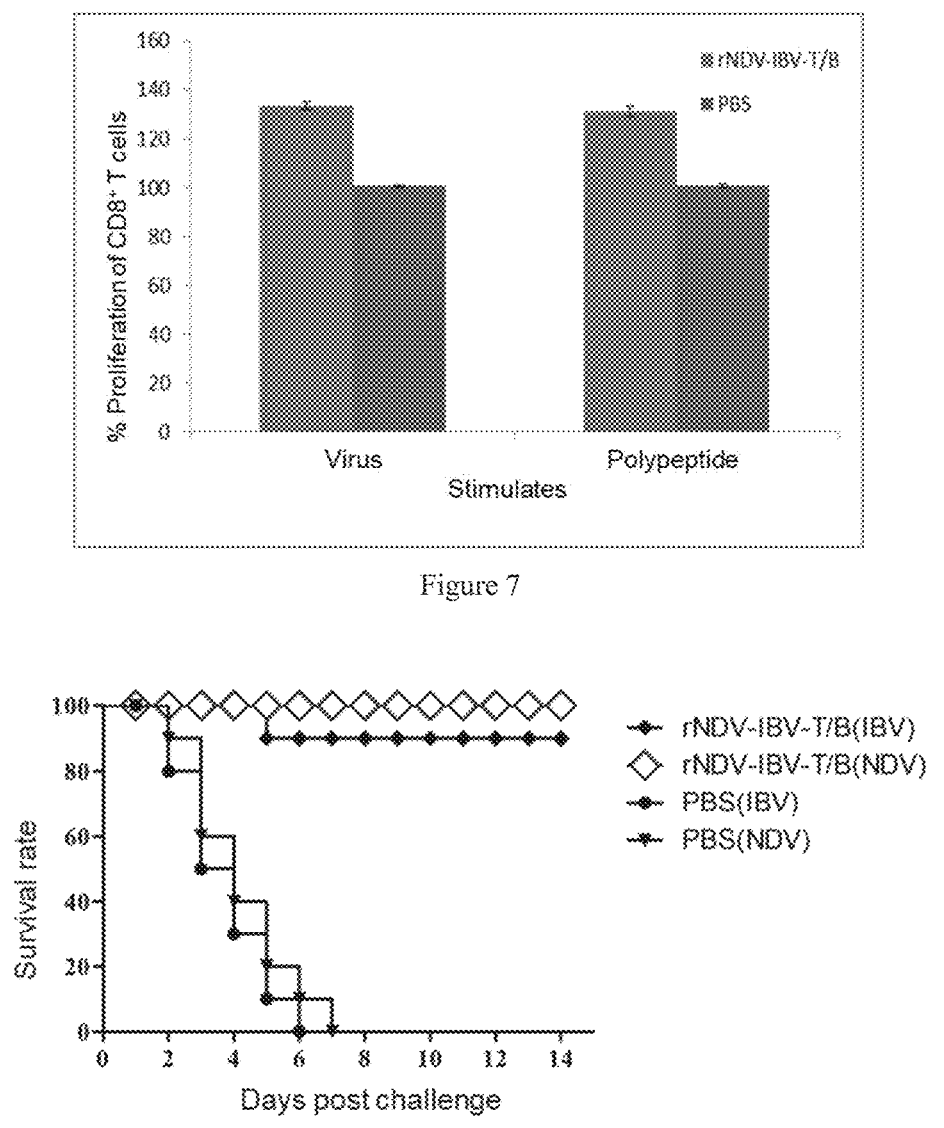

FIG. 7 shows analysis of $CD8^+$ T cell proliferation;

FIG. 8 shows protective efficacy against avian infectious bronchitis virus challenge.

DETAILED DESCRIPTION

The technical solutions of the present application are further described below by specific embodiments. It should be understood by those skilled in the art that the examples are only to facilitate to understand the present application and should not to be construed as specific limitations to the present application.

The experimental methods used in the following examples are conventional methods unless otherwise specified.

The materials, reagents and the like used in the following examples are commercially available unless otherwise specified.

Example 1

Construction of a Recombinant Plasmid Replaced with the HN Gene of TS09-C Strain and Inserted with a IBV S1-T/B Multi-Epitope and Virus Rescue Three pairs of primers SEQ ID NOs. 18-23 were designed according to the established whole genome sequence of TS09-C strain (GenBank accession number: JX110635.1). During the design of primers, a hepatitis D virus ribozyme sequence and a T7 RNA polymerase terminator sequence were introduced downstream of the 5' non-coding region, and a T7 RNA polymerase promoter sequence was introduced upstream of the 3' non-coding region, as shown in Table 1 below:

TABLE 1

| Primer Name | Primer Sequence (5' → 3') |
| --- | --- |
| SEQ ID NO. 18 | TAATACGACTCACTATAGGGAGAACCAAACAGAGAATCTGTGAGTTAC |
| SEQ ID NO. 19 | AACTCAGTGCCAACATGACTCGGAC |
| SEQ ID NO. 20 | TCCCGGTCGGCGCCTTCAAGGTGCA |
| SEQ ID NO. 21 | TCTGATGCTCCGCCCTCTCGGGACC |
| SEQ ID NO. 22 | AAAAATGTGGGTGGTAGCGGGATAT |
| SEQ ID NO. 23 | ACCAAACAAAGATTTGGTGAATGACAATAACTAGCATAACCCCTTGGGGCCTCTAAACGGGTCTTGATGGCCGGCATGGTCCCAGCCTCCTCGCTGGCGCCGGCTGGGCAACA |

Three overlapping whole genome cDNA fragments were amplified from allantoic fluid infected with LaSota strain virus, which were 1-4616 nt, 4517-8417 nt and 8318-15186 nt, respectively. The three cDNA fragments were stepwise connected to a clone vector pBR322 to obtain a full-length cDNA clone pBR-LS.

Figures 1, 2A, 2B, 2C:
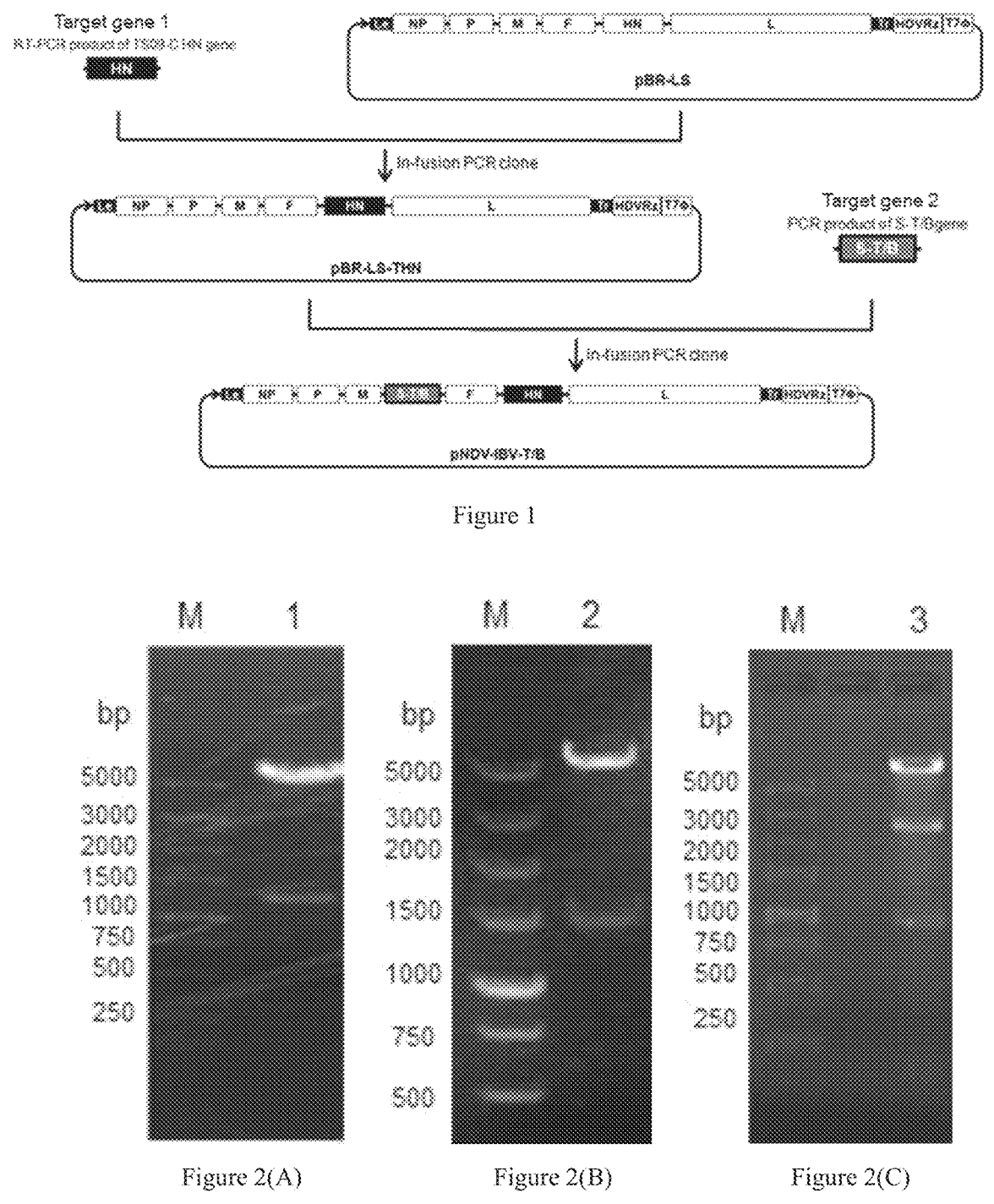

The HN gene was amplified from allantoic fluid infected with TS09-C strain virus by employing RT-PCR. The HN gene from TS09-C strain was integrated by fusion PCR and was used to replace the HN gene in pLS to obtain a plasmid pBR-LS-THN. In the same method, the multi-epitope chimeric S-T/B gene of avian infectious bronchitis virus was inserted between the M and F genes of LaSota strain to obtain a plasmid pNDV-IBV-T/B which had a plasmid profile as shown in FIG. 1.

The full-length sequences of NP, P and L genes of NDV LaSota strain were amplified separately by RT-PCR by using pLS plasmid as a PCR template and were ligated into a eukaryotic expression plasmid pVAX1 to obtain helper plasmids that could express proteins NDV NP, P and L, respectively, namely pVAX-NP, pVAX-P and pVAX-L.

Plasmid co-transfection was carried out by employing a calcium phosphate method. According to the instructions, four plasmids pNDV-IBV-T/B, pVAX-NP, pVAX-P and pVAX-L (mass ratio of 4:2:1:1) were co-transformed into BHK-21 cells that had been pre-infected with vTF7-3. After 6 h of transfection, cells were washed twice, and DMEM nutrient solution containing 1% of double antibiotics and 0.2 μg/mL TPCK-trypsin was added, followed by incubation for another 3 days. Repeated freeze-thaw was performed for 3 times and the cell culture was harvested. After removing the poxvirus vTF7-3 by filtration through a filter with a pore size of 0.22 μm, serial passage was performed in 9-11 day old SPF chicken embryos for 3 times, and then allantoic fluid was harvested for virus detection.

The infectious bronchitis virus S1 protein T and B cell epitope cassette IBV-T/B was inserted between P and M genes in the full-length cDNA backbone of LaSota strain containing the thermostable HN gene from TS09-C strain to obtain a recombinant plasmid pNDV-IBV-T/B. Electrophoresis after enzyme digestion of helper plasmid pVAX-P showed target fragments of 5.5 kb and 1.2 kb, electrophoresis after enzyme digestion of pVAX-NP with Xho I and Xba I showed two target fragments of 5.5 kb and 1.5 kb and digestion of pVAX-L with EcoR I showed three target fragments of 8.2 kb, 2.9 kb and 1.0 kb. Graphs of the restriction enzyme digestions were shown in FIG. 2(A)-FIG. 2(C).

The pNDV-IBV-T/B was co-transfected with three helper plasmids pVAX-NP, pVAX-P and pVAX-L (mass ratio of 4:2:1:1) into BHK-21 cells that had been pre-infected with vTF7-3, and then incubated for 72 hours. The supernatant was harvested, filtered, and was used to inoculate SPF chicken embryos. The allantoic fluid was collected, and RNA was extracted therefrom to reverse transcribe into cDNA. A RT-PCR amplification was performed with a upstream primer located at the P gene and a downstream primer located at the M gene to obtain PCR product of S-T/B with a size of 1365 bp. The PCR identification result was shown in FIG. 3. The sequencing result showed 100% matching with the expected sequence.

It was indicated that the T/B epitope sequence of infectious bronchitis virus had been inserted at the correct position of NDV, and an expected recombinant virus was obtained.

Example 2

Identification and Purification of Recombinant rNDV-IBV-T/B (I) Virus Titer and Growth Kinetics The virus titer of recombinant Newcastle disease vector live vaccine was determined by a HA test, a 50% tissue culture infective dose ($TCID_{50}$) assay on BHK-21 cells in the presence of 0.2 μg/ml TPCK-trypsin and a 50% egg infection dose ($EID_{50}$) assay in 10 day old SPF chicken embryos.

To determine the growth kinetics of recombinant virus, BHK-21 monolayer cells were infected with 0.1 MOI of recombinant Newcastle disease vector live vaccine for 1.5 hours, then washed with phosphate buffered saline (PBS) three times and covered with medium containing 2% fetal bovine serum (FBS). Supernatant was collected from the medium with infected cells at indicated time points and virus titration from the medium was performed by using a $TCID_{50}$ assay.

The following primers were designed based on the position of the replaced HN gene and the inserted S1-T/B epitope cassette: SEQ ID NOs. 24-25 were designed for TS09-C HN gene and SEQ ID NOs. 26-27 were designed for S1-T/B epitope cassette. The specific sequences are shown in Table 2:

TABLE 2

| Primer Name | Primer Sequence (5' → 3') |
| --- | --- |
| SEQ ID NO. 24 | ATGGACCGCGCAGTTAGCCAAGTTG |
| SEQ ID NO. 25 | TTATGGCCAACTGGCAGCGTAGGAC |

TABLE 2-continued

| Primer Name | Primer Sequence (5' → 3') |
| --- | --- |
| SEQ ID NO. 26 | CACTCGGCATCACACGGAATC |
| SEQ ID NO. 27 | GTCCACAAGTCAAGGCGCTG |

The specific PCR system is shown in Table 3 below, as follows:

TABLE 3

| | Reaction System | |
| --- | --- | --- |
| | Reagent Components | mx [μl] |
| PCR Reaction | PCR mix | 25 |
| | Upstream primer | 1 |
| | Downstream primer | 1 |
| | DNA template | 5 |
| | $ddH_2O$ | 18 |
| | Total | 50 |

The specific PCR conditions are shown in Table 4 below, as follows:

TABLE 4

| | Reaction Procedure | Number of Cycles |
| --- | --- | --- |
| Amplification Procedure | 94° C. 2 min | 1 |
| | 94° C. 30 s | 30 |
| | 55° C. 30 s | |
| | 68° C. 40 s | |
| | 72° C. 3 min | 1 |
| | 4° C. | 1 |

HN fragment and S1-T/B gene fragment were amplified.

II) Purification of Recombinant Virus

The virus strain which had been identified as positive and was a single plaque was used for purification. After digesting cells within the well containing this virus, half thereof was absorbed to dilute 100 times, and finally diluted into 10 ml with 2% FBS DMEM medium. The 10 ml of virus mixture was dispensed into a 96-well plate with 100 μl per well and incubated at 37° C., 5% $CO_2$ for 5 days. Then the 96-well plate was observed to select individual plaques for identification and storage.

III) Thermal Stability Test 1.0 ml of undiluted allantoic fluid containing recombinant Newcastle disease virus was sealed in a sterile vial. The sterile vial was immersed in a water bath at 56° C. and transferred to ice water at designated time points to stop the heat inactivation. The infectivity and HA activity of heat-inactivated recombinant Newcastle disease virus were titrated by performing a TCID50 assay and a standard HA assay in BHK-21 cells, respectively. Regression lines were plotted based on the infectivity and HA activity of virus over time and by monitoring recombinant Newcastle disease virus and parent strain LaSota at different time points. The time points of the heat-resistant virus for HA activity were 30, 60, 90 and 120 minutes, respectively.

In order to verify whether the rescued recombinant virus rNDV-IBV-T/B had similar heat-resistance characteristics to the parent TS09-C strain, a heat-resistance test was carried out for rTS09-C: the allantoic fluid from infected chicken embryo was placed in a water bath at 56° C. for heat treatment for 30, 60, 90 and 120 minutes, respectively, and then it was taken out and immediately placed in an ice bath. In order to determine whether the heat treated virus was still infectious, the heat-treated allantoic fluid was inoculated into SPF chicken embryos (5 embryos/sample). After 5 days of infection, the allantoic fluid was harvested for detection of HA activity. The results are shown in Table 5 below:

TABLE 5

| Strain Name | Heat treatment time/min | | | |
|---|---|---|---|---|
|  | 30 | 60 | 90 | 120 |
| TS09-C | + | + | − | − |
| LaSota | − | − | − | − |
| rNDV-IBV-T/B | + | + | + | − |

Note:
+ indicates infectious to chicken embryos; − indicates non-infectious to chicken embryos.

It can be seen from Table 5 that the TS09-C strain was still infectious after heat treatment at 56° C. for 60 min, and the period for rNDV-IBV-T/B strain was slightly longer, which was up to 90 min, while the LaSota strain was non-infectious after heat treatment for 30 min, indicating that the recombinant rNDV-IBV-T/B strain had heat-resistant properties.

IV) Observation by Transmission Electron Microscope (TEM)

The recombinant virus was largely propagated in 9-11 day old SPF chicken embryos. The harvested allantoic fluid was centrifuged at 2000 r/min for 20 min. Supernatant was collected and centrifuged at 28 000 r/min for 2 h. The supernatant was discarded and the precipitate was resuspended in PBS. The resuspended sample was added to the upper layer of 20%, 40%, 60% discontinuous density gradient of sucrose, centrifuged at 28000 r/min for 2.5 h, and 40-60% of intermediate protein layer was collected. The collected protein layer was diluted and mixed with PBS, and centrifuged at 28000 r/min for 2 h. The precipitate was resuspended in PBS, and 1 to 2 drops of resuspension were added to a copper mesh. After negative staining with tungsten phosphate, observed under TEM at 10,000 times magnification. The results are shown in FIG. 4.

Figure 4:
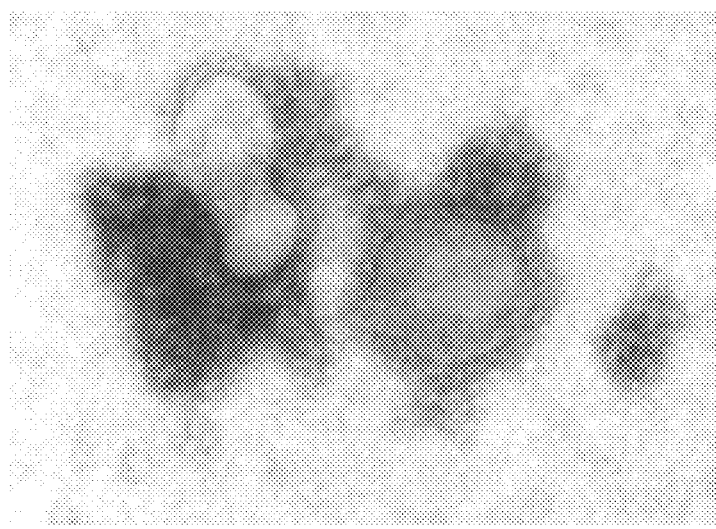
FIG. 4 is an electron micrograph of the recombinant virus rNDV-IBV-T/B.

It can be seen from FIG. 4 that the virion was in an irregular shape with non-fully identical size, about 200-300 nm in diameter, and a capsule located on the surface layer of virus can be clearly observed, which is consistent with the morphology of NDV. The above results fully demonstrated that the recombinant virus rNDV-IBV-T/B had been successfully rescued.

Example 3

Determination of Biological Characteristics of Recombinant rNDV-IBV-T/B

The above allantoic fluid that had been collected at each generation was subjected to determination of biological characteristics of the recombinant virus including mean death time of minimum lethal dose (MDT/MLD), intracerebral pathogenicity index (ICPI) virulence index and hemagglutination test (HA test) according to the OIE standard.

(I) MDT Assay 10 day old chicken embryos were taken. The vaccine was 10-fold serially diluted to five dilutions 10-7, 10-8, 10-9, 10-10, 10-11. 0.1 ml of each dilution was inoculated into the allantoic cavity of each of 5 SPF chicken embryos, and incubated in an incubator at 37.5° C. The eggs were irradiated twice a day for 7 consecutive days. Death time of each chicken embryo, minimum lethal dose which referred to the maximum dilution at which all inoculated chicken embryos were dead and MDT which was the mean time (h) required for the minimum lethal dose to kill all chicken embryos were recorded.

Time judgment criteria: immediate (acute/velogenic)<60 h, middle (subacute, mesogenic) 61-90 h, slow (low-virulence)>90 h. The results are shown in Tables 6-7:

TABLE 6

| Determination of minimum lethal dose | | | | | |
|---|---|---|---|---|---|
|  | $10^{-7}$ | $10^{-8}$ | $10^{-9}$ | $10^{-10}$ | $10^{-11}$ |
| LaSota | 5/5 | 5/5 | 3/5 | 1/5 | 0/5 |
| rNDV-IBV-T/B | 5/5 | 5/5 | 8/5 | 2/5 | 0/5 |

TABLE 7

| Determination of mean death time | | | | | | | | | |
|---|---|---|---|---|---|---|---|---|---|
|  | 1 | 2 | 3 | 4 | 5 | 6 | 7 | 8 | MDT |
| LaSota | 165 | 170 | 155 | 162 | 172 | 152 | 173 | 165 | 164.25 |
| rNDV-IBV-T/B | 166 | 153 | 169 | 155 | 152 | 172 | 168 | 159 | 161.75 |

It can be seen from Table 6 that the minimum lethal dose of recombinant Newcastle disease rNDV-IBV-T/B and its parent strain LaSota was $10^{-8}$ and it can be seen from Table 7 that the mean death time of recombinant Newcastle disease virus to chicken embryos at the minimum lethal dose was 161 hours, which was not significantly different from the parent strain.

(II) ICPI Assay

The recombinant NDV propagated from chicken embryo allantoic fluid was diluted 1:10 with sterile saline. 0.05 ml of each strain was inoculated intracerebrally into each of 8 susceptible chicks hatched 24-36 hours ago via a microsyringe (0.25 ml). A control group of 4 chicks was set up at the same time, and each chick was inoculated with 0.05 ml of sterile saline. Chickens were fed separately. The health status of chickens was observed every day at time points corresponding to the inoculation time, and the test chickens were evaluated: normal=0, sick=1, dead=2. Observed for 8 consecutive days, and the ICPI was finally obtained according to the equation. The specific results are shown in Table 8:

TABLE 8

Determination of intracerebral pathogenicity index in 1 day old chicks

| Strain | Symptoms after Inoculation | Number of Observation Days | | | | | | | | Total | Integration | ICPI |
|---|---|---|---|---|---|---|---|---|---|---|---|---|
| | | 1 | 2 | 3 | 4 | 5 | 6 | 7 | 8 | | | |
| LaSota | normal | 0 | 0 | 0 | 0 | 0 | 0 | 0 | 0 | 0 | 0 | 0 |
| | onset | 0 | 0 | 0 | 0 | 0 | 0 | 0 | 0 | 0 | 0 | |
| | death | 0 | 0 | 0 | 0 | 0 | 0 | 0 | 0 | 0 | 0 | |
| rNDV-IBV-T/B | normal | 0 | 0 | 0 | 0 | 0 | 0 | 0 | 0 | 0 | 0 | 0 |
| | onset | 0 | 0 | 0 | 0 | 0 | 0 | 0 | 0 | 0 | 0 | |
| | death | 0 | 0 | 0 | 0 | 0 | 0 | 0 | 0 | 0 | 0 | |

It can be seen from Table 8 that the recombinant virus had an intracerebral pathogenicity index of 0.00 in 1 day old SPF chickens.

Based on the results of Tables 6-8, it is clear that the recombinant Newcastle disease virus was an attenuated strain and was more safe.

(III) HA Assay

The red blood cells used were 1% chicken red blood cells freshly prepared according to a conventional method. Parent LaSota strain was used as a positive control in HA test and subjected to the same test. The HA test-positive allantoic fluid samples were diluted 1:100, 1:500, and 1:1000 times with 0.9% sterile saline, and then 0.2 mL of each dilution was used to inoculate each of 3 SPF chicken embryos. After culturing according to the above method, allantoic fluid was collected and also subjected to a HA test. The HA test-positive allantoic fluid samples were continued to being passaged in chicken embryos after appropriate dilution.

The recombinant Newcastle disease virus was passaged continuously for 25 generations in SPF chicken embryos, and mutations in nucleotide sequence of IBV-T/B epitope cassette was detected by RT-PCR and DNA sequencing. The results are shown in FIG. 5(A)-FIG. 5(B).

It can be seen from FIG. 5(A)-FIG. 5(B) that the IBV-T/B epitope cassette gene was still stably present after multiple passages without mutations in its bases, indicating a good genetic stability.

Example 4

Immunoprotective Efficacy of Recombinant rNDV-IBV-T/B

60 SPF chickens were randomly divided into 4 groups of 15 in each group. The specific groupings are shown in Table 9. Chickens were subjected to primary immunization at 7 day old and challenged with NDV and IBV at a dose of $5*10^5$ $ELD_{50}$ at 21 day old, specifically as follows:

TABLE 9

Experimental groupings and immunization procedures

| Group | Immunization Group | Immunization Dose | Immunization Route | Number of Immunizations |
|---|---|---|---|---|
| 1 | rNDV-IBV-T/B | $10^6$ $EID_{50}$ | Intranasal | 1 |
| 2 | rNDV-IBV-T/B | $10^6$ $EID_{50}$ | Intranasal | 1 |
| 3 | PBS | 200 μl | Intranasal | 1 |
| 4 | PBS | 200 μl | Intranasal | 1 |

(I) Detection of IgG Antibodies Specific for Avian Infectious Bronchitis Virus by ELISA Three chickens were randomly selected from each group to collect blood from the subpteryx vein prior to primary immunization and on 7 d, 14 d and 21 d after immunization, and serum was separated. The antibody titer was detected by an indirect ELISA method which was specifically as follows: The NDV and IBV virus solution were diluted 10-fold with coating solution, and then added to a microplate (100 μl/well) and incubated overnight at 4° C.; the liquid was discarded, the plate was washed 3 times with 300 μl of PBST per well and 3 min for each time, and 200 μl of 10% fetal bovine serum was added into per well to block, left at 37° C. for 2 h, and the plate was washed 3 times with PBST; the serum to be tested that had been diluted 20 times with PBS in advance was added (100 μl/well), placed at 37° C. for 2 h, and then the plate was washed 3 times with PBST; rabbit anti-chicken enzyme-labeled antibody IgG (1:5000 diluted with PBS) was added (100 μl/well), incubated at 37 h ° C. for 1 h, and then the plate was washed 3 times, 100 μl/well of TBM substrate solution was added, incubated at room temperature in dark for 20 min; 100 μl/well of 2N $H_2SO_4$ was added to terminate the reaction, and the OD values of each well was determined at a wavelength of 450 nm. The results are shown in FIG. 6.

It can be seen from FIG. 6 that the antibody level of vaccine group increased rapidly 7 days after the primary immunization, and reached the peak at 14 d, followed by a decrease and maintained at a high level. The vaccine immunization group was significantly higher than the PBS control group ($p<0.05$).

(II) Analysis of CD8+ T Lymphocyte Proliferation

Three chickens were randomly selected from each group to be euthanized. The spleens were isolated under sterile conditions and prepared into lymphocyte suspensions. The lymphocytes were stained with 1 ml of pre-warmed PBS containing 2.5 μM CFSE in a water bath at 37° C. for 10 minutes. After treatment, 0.2 mL FBS was used to terminate the reaction. The cell density was diluted to $10^6$ cells/ml with RPMI 1640 medium. The stained lymphocytes were divided into two groups and inoculated into 24-well plates at $10^6$ cells/well, respectively. The lymphocytes were stimulated with identified functional T cell epitope polypeptides (P8SRIQTATDP, P9SRNATGSQP, P18GAYAVVNV and P19SRIQTATQP) and avian infectious bronchitis virus, respectively, and cultured in an incubator at 37° C., 5% $CO_2$ for 5 days. The cultured lymphocytes were stained with PE-labeled mouse anti-chicken CD8 T cell monoclonal antibody. The proliferation ratio of $CD8^+$ T cells was detected by flow cytometry, and the proliferation rate was determined by CXP software. The proliferation rate of $CD8^+$ T cells of PBS control group after immunization was determined by flow cytometry and was set to 100% as normalization and used for comparison with immunization groups. The results are shown in FIG. 7.

It can be seen from FIG. 7 that the proliferation rate of $CD8^+$ T cells in rNDV-IBV-T/B group was 133.5±1.8% when stimulated with IBV, which was significantly higher than that in PBS group (100.5±0.6%) (p<0.05). The highest proliferation rate of T cells when stimulated and induced by mixed T cell epitope was also rNDV-IBV-T/B (131.1±0.7%), which was significantly higher than that of PBS control group pV-S1B (100.7±2.1%), exhibiting statistical difference (P<0.05). The results showed that the recombinant multi-epitope live vaccine rNDV-IBV-T/B was able to induce significant T lymphocyte proliferation in chickens.

Example 5

Protection Against Recombinant rNDV-IBV-T/B Challenge

Experimental method: A virus challenge was performed on the 7th day after booster immunization. Each chicken was challenged with $10^6$ $ELD_{50}$ of IBV Australian T strain via an intranasal route. After the challenge, the incidence of each group of chickens was observed for 10 consecutive days. The results are shown in FIG. 8.

It can be seen from FIG. 8 that the chickens in PBS group began to die on the 4th day after challenge with a mortality rate up to 100%. The lesions were mainly founded in respiratory tracts and kidneys after necropsy, with specific performance of mucus-filled upper respiratory tract, swollen throat, trachea with bleeding points, enlarged kidney, typical tinea kidney. After immunization with vaccine rNDV-IBV-T/B, the provided protective efficacy against NDV and IBV was 100% and 90%, respectively. It is thus obvious that the provided rNDV-IBV-T/B live vaccine can effectively resist the velogenic NDV and velogenic IBV challenges after immunization of SPF chickens with protection rates of 100% and 90%, respectively, proving that the vaccine was safe and effective.

In summary, in the present application, the multi-epitope chimeric ST/B gene of avian infectious bronchitis virus is inserted into the backbone of LaSota strain, so that the LaSota strain can express S1-T/B protein. Thus, the purpose of preventing both ND and IB diseases is achieved. In addition, the T cell epitopes and B cell epitopes can act synergistically to produce an earlier and more comprehensive immune response against virus. Moreover, in the present application, the HN gene of lentogenic TS09-C strain is replaced with that of the LaSota vaccine strain, increasing the thermal stability of LaSota strain without increasing its pathogenicity, and reducing the requirements for vaccine storage conditions and prolonging the shelf life.

The applicant states that the technological methods of the present application are illustrated in the present application through the embodiments described above, however, the present application is not limited to the technological procedures described above, i.e. it does not mean that the application must rely on the technological procedures described above to implement. It should be apparent to those skilled in the art that, for any improvement of the present application, the equivalent replacement of the selected raw materials of the present application, the addition of auxiliary components and the selection of specific methods, etc., all fall within the protection scope and the disclosure scope of the present application.

The invention claimed is:

1. A composite multi-epitope expression cassette comprising:
   (a) T cell epitopes derived from S1 proteins of avian infectious bronchitis virus Holte strain and avian infectious bronchitis virus QX-like strain; and
   (b) B cell epitopes derived from S1 protein of avian infectious bronchitis virus Australian T strain.

2. The composite multi-epitope expression cassette according to claim 1, wherein the T cell epitopes have amino acid sequences as shown in SEQ ID NOs. 1-4.

3. The composite multi-epitope expression cassette according to claim 2, wherein the B cell epitopes have amino acid sequences as shown in SEQ ID NOs. 5-7.

4. The composite multi-epitope expression cassette according to claim 2, wherein different epitopes among the T cell epitopes and the B cell epitopes are linked by a flexible small molecule linker.

5. The composite multi-epitope expression cassette according to claim 1, wherein an enzyme cleavage site is further included in front of and behind the expression cassette.

6. A recombinant virus comprising a gene encoding the composite multi-epitope expression cassette according to claim 1.

7. A composite multi-epitope vaccine comprising the recombinant virus according to claim 6.

8. A method for treating Newcastle disease and/or avian infectious bronchitis in a chicken, comprising administrating an effective amount of the composite multi-epitope vaccine according to claim 7 to the chicken.

9. The composite multi-epitope expression cassette according to claim 4, wherein the flexible small molecule linker is KAA, AAY, AAA, GAAA, KAAA, and has the nucleotide sequence as shown in SEQ ID NOs. 8-12.

10. The composite multi-epitope expression cassette according to claim 5, wherein the cleavage site is any one of Spe I, Xho I, BamH I, EcoR I, Nde I, Pst I or Xho I.

11. The composite multi-epitope expression cassette according to claim 1, wherein a KOZAK sequence which has the nucleotide sequence as shown in SEQ ID NO. 13 is further included behind the cleavage site that is located in front of the expression cassette.

12. The composite multi-epitope expression cassette according to claim 1, wherein the expression cassette has the amino acid sequence as shown in SEQ ID NO. 14 and the nucleotide sequence as shown in SEQ ID NO. 15.

* * * * *

SEQUENCE LISTING

```
<160> NUMBER OF SEQ ID NOS: 27

<210> SEQ ID NO 1
<211> LENGTH: 8
<212> TYPE: PRT
<213> ORGANISM: Avian infectious bronchitis virus

<400> SEQUENCE: 1

Gly Ala Tyr Ala Val Val Asn Val
1               5

<210> SEQ ID NO 2
<211> LENGTH: 9
<212> TYPE: PRT
<213> ORGANISM: Avian infectious bronchitis virus

<400> SEQUENCE: 2

Ser Arg Ile Gln Thr Ala Thr Gln Pro
1               5

<210> SEQ ID NO 3
<211> LENGTH: 9
<212> TYPE: PRT
<213> ORGANISM: Avian infectious bronchitis virus
```

<400> SEQUENCE: 3

Ser Arg Ile Gln Thr Ala Thr Asp Pro
1               5

<210> SEQ ID NO 4
<211> LENGTH: 9
<212> TYPE: PRT
<213> ORGANISM: Avian infectious bronchitis virus

<400> SEQUENCE: 4

Ser Arg Asn Ala Thr Gly Ser Gln Pro
1               5

<210> SEQ ID NO 5
<211> LENGTH: 37
<212> TYPE: PRT
<213> ORGANISM: Avian infectious bronchitis virus

<400> SEQUENCE: 5

Asn Tyr Val Tyr Tyr Gln Ser Ala Phe Arg Pro Ser Gly Gly Trp
1               5                   10                  15

His Leu His Gly Gly Ala Tyr Ala Val Val Asn Val Ser Gln Glu Thr
            20                  25                  30

Ser Asn Ala Gly Ser
        35

<210> SEQ ID NO 6
<211> LENGTH: 17
<212> TYPE: PRT
<213> ORGANISM: Avian infectious bronchitis virus

<400> SEQUENCE: 6

Arg Ile Ala Ala Met Lys Gln Gly Gly Asn Gly Pro Ser Asp Leu Phe
1               5                   10                  15

Tyr

<210> SEQ ID NO 7
<211> LENGTH: 107
<212> TYPE: PRT
<213> ORGANISM: Avian infectious bronchitis virus

<400> SEQUENCE: 7

Gln Thr Tyr Gln Thr Gln Thr Ala Gln Ser Gly Tyr Tyr Asn Phe Asn
1               5                   10                  15

Phe Ser Phe Leu Ser Gly Phe Val Tyr Lys Glu Phe Asn Phe Met Tyr
            20                  25                  30

Gly Ser Tyr His Pro Lys Cys Asn Phe Arg Pro Glu Asn Ile Asn Asn
        35                  40                  45

Gly Leu Trp Phe Asn Ser Leu Ser Val Ser Leu Ala Tyr Gly Pro Leu
    50                  55                  60

Gln Gly Gly Cys Lys Gln Ser Val Phe His Gly Arg Ala Thr Cys Cys
65                  70                  75                  80

Tyr Ala Tyr Ser Tyr Leu Gly Pro Arg Leu Cys Lys Gly Val Tyr Ser
                85                  90                  95

Gly Glu Leu Thr Gln Gln Phe Glu Cys Gly Leu
            100                 105

<210> SEQ ID NO 8
<211> LENGTH: 9

```
<212> TYPE: DNA
<213> ORGANISM: Artificial sequence
<220> FEATURE:
<223> OTHER INFORMATION: linker sequence

<400> SEQUENCE: 8 aaagctgct                                                               9

<210> SEQ ID NO 9
<211> LENGTH: 9
<212> TYPE: DNA
<213> ORGANISM: Artificial sequence
<220> FEATURE:
<223> OTHER INFORMATION: linker sequence

<400> SEQUENCE: 9 gccgcatac                                                               9

<210> SEQ ID NO 10
<211> LENGTH: 9
<212> TYPE: DNA
<213> ORGANISM: Artificial sequence
<220> FEATURE:
<223> OTHER INFORMATION: linker sequence

<400> SEQUENCE: 10 gctgccgcc                                                               9

<210> SEQ ID NO 11
<211> LENGTH: 12
<212> TYPE: DNA
<213> ORGANISM: Artificial sequence
<220> FEATURE:
<223> OTHER INFORMATION: linker sequence

<400> SEQUENCE: 11
ggcgcagcag cc                                                          12

<210> SEQ ID NO 12
<211> LENGTH: 12
<212> TYPE: DNA
<213> ORGANISM: Artificial sequence
<220> FEATURE:
<223> OTHER INFORMATION: linker sequence

<400> SEQUENCE: 12
aaagcagccg ca                                                          12

<210> SEQ ID NO 13
<211> LENGTH: 9
<212> TYPE: DNA
<213> ORGANISM: Artificial sequence
<220> FEATURE:
<223> OTHER INFORMATION: linker sequence

<400> SEQUENCE: 13 gccaccatg                                                               9

<210> SEQ ID NO 14
<211> LENGTH: 331
<212> TYPE: PRT
<213> ORGANISM: Artificial sequence
<220> FEATURE:
<223> OTHER INFORMATION: Amino acid sequence of the expression cassette
      of the present application

<400> SEQUENCE: 14
```

Met Gly Asn Tyr Val Tyr Tyr Gln Ser Ala Phe Arg Pro Ser Gly
1               5                   10                  15

Gly Trp His Leu His Gly Gly Ala Tyr Ala Val Val Asn Val Ser Gln
            20                  25                  30

Glu Thr Ser Asn Ala Gly Ser Gly Gly Gly Ser Gly Gly Gly Gly
            35                  40                  45

Ser Gly Gly Gly Ser Arg Ile Ala Ala Met Lys Gln Gly Gly Asn
50                  55                  60

Gly Pro Ser Asp Leu Phe Tyr Gly Gly Gly Ser Gly Gly Gly Gly
65              70                  75                  80

Ser Gly Gly Gly Ser Gln Thr Tyr Gln Thr Gln Thr Ala Gln Ser
            85                  90                  95

Gly Tyr Tyr Asn Phe Asn Phe Ser Phe Leu Ser Gly Phe Val Tyr Lys
                100                 105                 110

Glu Phe Asn Phe Met Tyr Gly Ser Tyr His Pro Lys Cys Asn Phe Arg
            115                 120                 125

Pro Glu Asn Ile Asn Asn Gly Leu Trp Phe Asn Ser Leu Ser Val Ser
            130                 135                 140

Leu Ala Tyr Gly Pro Leu Gln Gly Gly Cys Lys Gln Ser Val Phe His
145                 150                 155                 160

Gly Arg Ala Thr Cys Cys Tyr Ala Tyr Ser Tyr Leu Gly Pro Arg Leu
                165                 170                 175

Cys Lys Gly Val Tyr Ser Gly Glu Leu Thr Gln Gln Phe Glu Cys Gly
                180                 185                 190

Leu Thr Ser Asn Phe Asp Leu Leu Lys Leu Ala Gly Asp Val Glu Ser
            195                 200                 205

Asn Pro Gly Pro Phe Phe Phe Met Gln Val Gln Ile Gln Ser Leu Phe
            210                 215                 220

Leu Leu Leu Leu Trp Val Pro Gly Ser Arg Gly Lys Ala Ala Gly Ala
225                 230                 235                 240

Tyr Ala Val Val Asn Val Ala Ala Ala Ser Arg Ile Gln Thr Ala Thr
                245                 250                 255

Gln Pro Ala Ala Tyr Ser Arg Asn Glu Thr Asp Ser Gln Pro Gly Ala
            260                 265                 270

Ala Ala Ser Arg Asn Ala Thr Gly Ser Gln Pro Lys Ala Ala Gly Ala
            275                 280                 285

Tyr Ala Val Val Asn Val Ala Ala Ala Ser Arg Ile Gln Thr Ala Thr
            290                 295                 300

Gln Pro Ala Ala Tyr Ser Arg Asn Glu Thr Asp Ser Gln Pro Gly Ala
305                 310                 315                 320

Ala Ala Ser Arg Asn Ala Thr Gly Ser Gln Pro
            325                 330

<210> SEQ ID NO 15
<211> LENGTH: 1032
<212> TYPE: DNA
<213> ORGANISM: Artificial sequence
<220> FEATURE:
<223> OTHER INFORMATION: Nucleotide sequence of the expression cassette
      of the present application

<400> SEQUENCE: 15
acgggtagaa agcttgccac catgggaaat tacgtttact actaccaaag tgccttcaga       60
ccatcaggtg gttggcattt acatggaggt gcttatgcag tagtaaatgt ttcgcaagaa      120

```
accagtaatg caggaagcgg aggcggaggc tccggaggag gaggctccgg aggcggaggg    180
tctcgtattg ctgccatgaa gcaaggcggt aatgggccta gtgatttatt ttatggaggc    240
ggaggctccg gaggaggagg ctccggaggc ggagggtctc aaacttatca acacaaaca    300 gctcagagtg gttattataa ttttaacttc tcatttctga gtggttttgt gtataaggag    360
tttaatttta tgtatggttc ttatcaccca aagtgtaatt ttagaccaga aaacattaat    420
aatggcctct ggtttaattc actttcagtt tcgcttgcgt atggccctct tcaaggcggc    480
tgcaagcaat ctgtctttca tggtagagca acttgctgtt atgcctactc ctatttaggt    540
cctaggttat gtaaaggtgt ttatagtggt gagttaacac agcagtttga atgtggactg    600
actagtaact ttgacctgct caagttggca ggagacgtcg agtccaaccc tgggcctttc    660
ttcttcatgc aggtgcagat ccagagcctg tttctgctcc tcctgtgggt gcccggctcc    720
agaggaaaag ctgctggtgc atatgcagtc gtcaacgttg ctgccgccag taggattcag    780
acggctactc agccgccgc atacagtaga aatgagaccg atagtcagcc gggcgcagca    840
gccagtagaa acgctactgg tagtcaaccg aaagctgctg gtgcatatgc agtcgtcaac    900
gttgctgccg ccagtaggat tcagacggct actcagccgg ccgcatacag tagaaatgag    960
accgatagtc agccgggcgc agcagccagt agaaacgcta ctggtagtca accgtaataa   1020
ttaagaaaaa at                                                        1032
```

<210> SEQ ID NO 16
<211> LENGTH: 616
<212> TYPE: PRT
<213> ORGANISM: Newcastle disease virus TS09-C strain

<400> SEQUENCE: 16

Met Asp Arg Ala Val Ser Gln Val Ala Leu Glu Asn Asp Glu Arg Glu
1               5                   10                  15

Ala Lys Asn Thr Trp Arg Leu Val Phe Arg Ile Ala Ile Leu Leu Ser
            20                  25                  30

Thr Val Val Thr Leu Ala Ile Ser Ala Ala Ala Leu Ala Tyr Ser Met
        35                  40                  45

Glu Ala Ser Thr Pro Ser Asp Leu Val Gly Ile Pro Thr Ala Ile Ser
    50                  55                  60

Arg Ala Glu Glu Lys Ile Thr Ser Ala Leu Gly Ser Asn Gln Asp Val
65                  70                  75                  80

Val Asp Arg Ile Tyr Lys Gln Val Ala Leu Glu Ser Pro Leu Ala Leu
                85                  90                  95

Leu Asn Thr Glu Ser Thr Ile Met Asn Ala Ile Thr Ser Leu Ser Tyr
            100                 105                 110

Gln Ile Ser Gly Ala Ala Ser Ser Ser Gly Cys Gly Ala Pro Ile His
        115                 120                 125

Asp Pro Asp Tyr Ile Gly Gly Ile Gly Lys Glu Leu Ile Val Asp Asp
    130                 135                 140

Ala Ser Asp Val Thr Ser Tyr Tyr Pro Ser Ala Phe Gln Glu His Leu
145                 150                 155                 160

Asn Phe Ile Pro Ala Pro Thr Thr Gly Ser Gly Cys Thr Arg Met Pro
                165                 170                 175

Ser Phe Asp Met Ser Ala Thr His Tyr Cys Tyr Thr His Asn Val Ile
            180                 185                 190

Leu Ser Gly Cys Arg Asp His Ser His Ser His Gln Tyr Leu Ala Leu
        195                 200                 205

```
Gly Val Leu Arg Thr Ser Ala Thr Gly Arg Val Phe Phe Ser Thr Leu
    210                 215                 220
Arg Ser Ile Asn Leu Asp Asp Thr Gln Asn Arg Lys Ser Cys Ser Val
225                 230                 235                 240
Ser Ala Thr Pro Leu Gly Cys Asp Met Leu Cys Ser Lys Val Thr Glu
                245                 250                 255
Thr Glu Glu Glu Asp Tyr Asn Ser Ala Ile Pro Thr Ser Met Val His
                260                 265                 270
Gly Arg Leu Gly Phe Asp Gly Gln Tyr His Glu Lys Asp Leu Asp Val
                275                 280                 285
Thr Thr Leu Phe Glu Asp Trp Val Ala Asn Tyr Pro Gly Val Gly Gly
290                 295                 300
Gly Ser Phe Ile Asp Asn Arg Val Trp Phe Pro Val Tyr Gly Gly Leu
305                 310                 315                 320
Lys Pro Asn Ser Pro Ser Asp Thr Ala Gln Glu Gly Lys Tyr Val Ile
                325                 330                 335
Tyr Lys Arg Tyr Asn Asp Thr Cys Pro Asp Glu Gln Asp Tyr Gln Ile
                340                 345                 350
Gln Met Ala Lys Ser Ser Tyr Lys Pro Gly Arg Phe Gly Gly Lys Arg
                355                 360                 365
Val Gln Gln Ala Val Leu Ser Ile Lys Val Ser Thr Ser Leu Gly Glu
370                 375                 380
Asp Pro Val Leu Thr Val Pro Pro Asn Thr Val Thr Leu Met Gly Ala
385                 390                 395                 400
Glu Gly Arg Val Leu Thr Val Gly Thr Ser His Phe Leu Tyr Gln Arg
                405                 410                 415
Gly Ser Ser Tyr Phe Ser Pro Ala Leu Leu Tyr Pro Met Ile Val Ser
                420                 425                 430
Asn Lys Thr Ala Thr Leu His Ser Pro Tyr Thr Phe Asn Ala Phe Thr
                435                 440                 445
Arg Pro Gly Ser Val Pro Cys Gln Ala Ser Ala Arg Cys Pro Asn Ser
                450                 455                 460
Cys Val Thr Gly Val Tyr Thr Asp Pro Tyr Pro Leu Val Phe Tyr Arg
465                 470                 475                 480
Asn His Thr Leu Arg Gly Val Phe Gly Thr Met Leu Asp Asp Lys Gln
                485                 490                 495
Ala Arg Leu Asn Pro Val Ser Ala Val Phe Asp Ser Ile Ser Arg Ser
                500                 505                 510
Arg Ile Thr Arg Val Ser Ser Ser Thr Lys Ala Ala Tyr Thr Thr
                515                 520                 525
Ser Thr Cys Phe Lys Val Val Lys Thr Asn Lys Thr Tyr Cys Leu Ser
530                 535                 540
Ile Ala Glu Ile Ser Asn Thr Leu Phe Gly Glu Phe Arg Ile Val Pro
545                 550                 555                 560
Leu Leu Val Glu Ile Leu Lys Asp Asp Gly Val Arg Glu Ala Arg Ser
                565                 570                 575
Ser Arg Leu Ser Gln Leu Arg Glu Gly Trp Lys Asp Asp Ile Val Ser
                580                 585                 590
Pro Ile Phe Cys Asp Ala Lys Asn Gln Thr Glu Tyr Arg His Glu Leu
                595                 600                 605
Glu Ser Tyr Ala Ala Ser Trp Pro
610                 615
```

<210> SEQ ID NO 17
<211> LENGTH: 2002
<212> TYPE: DNA
<213> ORGANISM: Newcastle disease virus TS09-C strain

<400> SEQUENCE: 17

```
acgggtagaa cggtcgggga ggccgtccct caatcgggag ccgggcctca caacatccgt    60
tctaccgcat caccaatagc agttttcagt catggaccgc gcagttagcc aagttgcgct   120
agagaatgat gaaagagagg caaagaatac atggcgcttg gtattccgga tcgcaatcct   180
actctcaacg gtggtgacct tagccatctc tgcagccgcc cttgcatata gcatggaggc   240
cagcacacct agcgatcttg taggcatacc gactgcgatc tctagagcag aggaaaagat   300
tacatctgca ctcggttcca atcaagatgt agtagatagg atatataagc aggtggccct   360
cgaatctcca ctggcattgc taaacaccga atctacaatt atgaacgcaa taacgtctct   420
ctcttatcaa atcagtgggg ccgcaagtag cagcggatgt ggagcaccca ttcatgatcc   480
agattatatt ggaggaatag gtaaagaact tattgtagat gatgctagcg acgtcacatc   540
atactatccc tctgcgttcc aagaacacct gaactttatc ccggcgccta ctacaggatc   600
aggttgcact cggatgccct catttgacat gagcgctacc cactactgtt atactcacaa   660
tgtgatatta tctggctgca gagatcactc gcactcacat caatatttag cacttggtgt   720
gcttcggaca tctgcaacag ggagggtatt cttttccact ctgcgttcca tcaatctgga   780
tgacacccaa atcggaagtc ttgcagtgt gagtgcaacc cccttgggtt gtgatatgct   840
gtgctctaaa gtcacagaga ctgaagaaga ggattataac tcagctatcc ccacgtcgat   900
ggtacatgga aggttagggt tcgacggcca ataccacgag aaggacctag atgtcacaac   960
actattcgag gactgggtgg caaactaccc aggagtagga ggcgggtctt ttattgacaa  1020
ccgcgtatgg ttcccagttt acgggggct aaaacccaat tcgcccagtg acaccgcaca  1080
agaagggaaa tatgtaatat acaagcgata caatgacaca tgtccagatg agcaagatta  1140
tcagattcaa atggctaagt cttcatataa gcctgggcgg tttggaggga aacgcgtaca  1200
gcaggccgtc ttatctatca aagtgtcaac atccttgggc gaggacccgg tgctgactgt  1260
accgcccaac acagtaacac tcatgggggc cgaaggcaga gttctcacag tagggacatc  1320
tcatttcctt tatcagcgag ggtcatcata cttctcccct gccctactat atcctatgat  1380
agtcagcaac aaaacagcca ctcttcatag tccttataca ttcaatgcct tcactcgacc  1440
aggtagtgtc ccttgccagg cttcagcaag atgccctaac tcatgtgtta ccggagtcta  1500
tactgatcca tatcccttgg tcttctatag gaaccacacc ttgcgagggg tattcgggac  1560
gatgcttgat gataaacaag caagactcaa ccctgtatct gcagtatttg acagcatatc  1620
ccgcagtcgc ataacccggg tgagttcaag cagcaccaag gcagcataca caacatcaac  1680
atgttttaaa gttgtaaaga ccaataaaac ctattgtctc agcattgccg aaatatccaa  1740
taccctcttc ggggaattca gaatcgtccc tttactagtt gagattctca aggatgatgg  1800
ggttagagaa gccaggtcta gccggttgag tcaactgcga gagggttgga agatgacat  1860
tgtatcacct atcttttgcg acgccaagaa tcaaactgaa taccggcacg agctcgagtc  1920
ctacgctgcc agttggccat aatcagctag tgctaatgtg attagattaa gtcttgtcgg  1980
tagtcacttg attaagaaaa aa                                            2002
```

<210> SEQ ID NO 18
<211> LENGTH: 48
<212> TYPE: DNA

```
<213> ORGANISM: Artificial sequence
<220> FEATURE:
<223> OTHER INFORMATION: Primer

<400> SEQUENCE: 18
taatacgact cactataggg agaaccaaac agagaatctg tgagttac        48

<210> SEQ ID NO 19
<211> LENGTH: 25
<212> TYPE: DNA
<213> ORGANISM: Artificial sequence
<220> FEATURE:
<223> OTHER INFORMATION: Primer

<400> SEQUENCE: 19
aactcagtgc caacatgact cggac                                 25

<210> SEQ ID NO 20
<211> LENGTH: 25
<212> TYPE: DNA
<213> ORGANISM: Artificial sequence
<220> FEATURE:
<223> OTHER INFORMATION: Primer

<400> SEQUENCE: 20
tcccggtcgg cgccttcaag gtgca                                 25

<210> SEQ ID NO 21
<211> LENGTH: 25
<212> TYPE: DNA
<213> ORGANISM: Artificial sequence
<220> FEATURE:
<223> OTHER INFORMATION: Primer

<400> SEQUENCE: 21
tctgatgctc cgccctctcg ggacc                                 25

<210> SEQ ID NO 22
<211> LENGTH: 25
<212> TYPE: DNA
<213> ORGANISM: Artificial sequence
<220> FEATURE:
<223> OTHER INFORMATION: Primer

<400> SEQUENCE: 22
aaaaatgtgg gtggtagcgg gatat                                 25

<210> SEQ ID NO 23
<211> LENGTH: 113
<212> TYPE: DNA
<213> ORGANISM: Artificial sequence
<220> FEATURE:
<223> OTHER INFORMATION: Primer

<400> SEQUENCE: 23
accaaacaaa gatttggtga atgacaataa ctagcataac ccettggggc ctctaaacgg   60 gtcttgatgg ccggcatggt cccagcctcc tcgctggcgc cggctgggca aca         113

<210> SEQ ID NO 24
<211> LENGTH: 25
<212> TYPE: DNA
<213> ORGANISM: Artificial sequence
<220> FEATURE:
<223> OTHER INFORMATION: Primer

<400> SEQUENCE: 24
```

```
atggaccgcg cagttagcca agttg                                          25

<210> SEQ ID NO 25
<211> LENGTH: 25
<212> TYPE: DNA
<213> ORGANISM: Artificial sequence
<220> FEATURE:
<223> OTHER INFORMATION: Primer

<400> SEQUENCE: 25
ttatggccaa ctggcagcgt aggac                                          25

<210> SEQ ID NO 26
<211> LENGTH: 21
<212> TYPE: DNA
<213> ORGANISM: Artificial sequence
<220> FEATURE:
<223> OTHER INFORMATION: Primer

<400> SEQUENCE: 26
cactcggcat cacacggaat c                                              21

<210> SEQ ID NO 27
<211> LENGTH: 20
<212> TYPE: DNA
<213> ORGANISM: Artificial sequence
<220> FEATURE:
<223> OTHER INFORMATION: Primer

<400> SEQUENCE: 27
gtccacaagt caaggcgctg                                                20
```